United States Patent
Burz et al.

(10) Patent No.: US 8,684,003 B2
(45) Date of Patent: Apr. 1, 2014

(54) BREATHING MASK DEVICE AND METHOD AND MOLD FOR PRODUCING SAME

(75) Inventors: Johann S. Burz, Germaringen (DE);
Achim Biener, Aufkirchen (DE); Bernd Lang, Gräfelfing (DE)

(73) Assignee: Resmed R&D Germany GmbH, Martinsried (DE)

( * ) Notice: Subject to any disclaimer, the term of this patent is extended or adjusted under 35 U.S.C. 154(b) by 1582 days.

(21) Appl. No.: 11/988,503

(22) PCT Filed: Jul. 19, 2006

(86) PCT No.: PCT/EP2006/007121
§ 371 (c)(1),
(2), (4) Date: Jan. 9, 2008

(87) PCT Pub. No.: WO2007/009782
PCT Pub. Date: Jan. 25, 2007

(65) Prior Publication Data
US 2009/0078267 A1 Mar. 26, 2009

(30) Foreign Application Priority Data

Jul. 19, 2005 (DE) .......................... 10 2005 033 648
Jul. 19, 2005 (DE) .......................... 10 2005 033 650

(51) Int. Cl.
*A61M 11/00* (2006.01)
(52) U.S. Cl.
USPC ............. 128/206.24; 128/205.25; 128/206.21
(58) Field of Classification Search
USPC ............. 128/206.21, 206.24, 206.25, 206.26, 128/206.28, 207.13, 112.1, 117.1, 118.1, 128/120.1
See application file for complete search history.

(56) References Cited

U.S. PATENT DOCUMENTS 5,079,786 A * 1/1992 Rojas ................................. 5/654
5,800,402 A * 9/1998 Bierman ....................... 604/180
(Continued)

FOREIGN PATENT DOCUMENTS

| EP | 1 099 452 | 5/2001 |
|---|---|---|
| EP | 1 360 971 | 11/2003 |
| GB | 790 677 | 2/1958 |
| WO | 03/035156 | 5/2003 |
| WO | 03/105921 | 12/2003 |
| WO | 2004/078231 | 9/2004 |

OTHER PUBLICATIONS

Lang et al., (EP 1099452 A2), English language translation provided by the European Patent Office, whole document.*

(Continued)

*Primary Examiner* — Steven Douglas
(74) *Attorney, Agent, or Firm* — Nixon & Vanderhye, P.C.

(57) ABSTRACT

A breathing mask device, a sealing lip device for a breathing mask device, a molding tool and a method for producing a corresponding breathing mask device and sealing lip device are described. An aspect of the invention is to provide ways that make it possible to create a breathing mask device that, with sufficiently strong tightness is distinguished by particular wearing comfort and which moreover can be produced advantageously in times of industrial production standpoints. According to an embodiment, a breathing mask device for administering a breathable gas is provided and includes a body structure that is sealed against a contact surface of a user's face, a sealing lip device that in combination with the body structure in part defines a breathing mask interior, a gel structure for at least intermittent and partial transmission of the retention forces, acting on the body structure, to the user's face area, and a gel material defining the gel structure is received in a gel receiving chamber defined at least in part by an elastically deformable receiving wall. The elastomer material intended for forming the receiving wall is integrally formed onto a wall portion of the breathing mask device, and is lifted or separated from this wall portion to form the gel receiving chamber.

36 Claims, 11 Drawing Sheets

(56) References Cited

U.S. PATENT DOCUMENTS

| | | | |
|---|---|---|---|
| 6,152,137 | A | 11/2000 | Schwartz et al. |
| 6,196,223 | B1 | 3/2001 | Belfer et al. |
| 6,397,847 | B1 | 6/2002 | Scarberry et al. |
| 6,408,853 | B1 | 6/2002 | Chang |
| 2003/0196657 | A1 | 10/2003 | Ging et al. |
| 2003/0221691 | A1 | 12/2003 | Biener et al. |
| 2004/0149287 | A1* | 8/2004 | Namey, Jr. ............... 128/205.25 |
| 2005/0076912 | A1 | 4/2005 | Eifler et al. |
| 2005/0199239 | A1* | 9/2005 | Lang et al. ............... 128/206.24 |

OTHER PUBLICATIONS

Japanese Office Action for corresponding Japanese Application No. 2008-521886, mailed Aug. 9, 2011 (6 pages).
International Search Report for PCT/EP2006/007121 mailed Dec. 1, 2006.
Written Opinion for PCT/EP2006/007121 mailed Dec. 1, 2006.

* cited by examiner

BREATHING MASK DEVICE AND METHOD AND MOLD FOR PRODUCING SAME

CROSS-REFERENCES TO RELATED APPLICATIONS

This application is the U.S. national phase of International Application No. PCT/EP2006/007121 filed 19 Jul. 2006 which designated the U.S. and claims priority to German Patent Application Nos. 10 2005 033 648.5 and 10 2005 033 650.7 filed 19 Jul. 2005, the entire contents of each of which are hereby incorporated by reference.

BACKGROUND OF THE INVENTION

The invention is directed to a breathing mask device, a sealing lip device for a breathing mask device, as well as to a molding tool and a method for producing a corresponding breathing mask device and sealing lip device.

Breathing mask arrangements are used particularly for administering a breathable gas mixture, such as ambient air, at a pressure level that is above ambient pressure. Delivering the breathing gas at a pressure level above the ambient pressure can be used for instance for performing so-called CPAP therapy for treating stroke- or sleep-related respiratory disturbances.

From International Patent Application PCT/EP02/11798, incorporated herein by reference in its entirety and filed by the present Applicant, a breathing mask device for administering a breathable gas to a user is known. This breathing mask device makes it possible, in cooperation with the face area of a user of the mask, to seal off a mask interior of the breathing mask from the environment. Such breathing masks are used particularly in conjunction with medical or therapeutic administration of breathable gases, as well as in the industrial field, for instance in the field of gas masks and breathing equipment. Typically in these breathing masks, the sealing off from the face area of the breathing mask user is achieved using a sealing lip structure that extends, oriented inward, around an opening in the mask and is seated on the face area and is made from an elastically deformable material. The sealing action achieved with such sealing lips generally increases with the contact pressure of the sealing lip against the face area. In the case of high contact pressures, long-term use of such breathing masks in particular can be unpleasant. A need in the art has developed to address this problem.

BRIEF SUMMARY OF THE INVENTION

An aspect of the invention is to provide ways that make it possible to create a breathing mask device which while being sufficiently nonleaking is distinguished by being especially comfortable to wear and moreover can be produced advantageously in times of industrial production.

According to one embodiment or example of the invention, there is provided a breathing mask device for administering a breathable gas, having a body structure, which in the application position is pressed with a sufficient retention force against a contact surface of a user's face, a sealing lip device that in cooperation with the body structure and the portion of the user's face defines a breathing mask interior and seals it off from the environment, a gel structure for at least intermittent and partial transmission of the retention forces, acting on the body structure, to the user's face area, and a gel material defining the gel structure is received in a gel receiving chamber defined at least in part by an elastically deformable receiving wall. The elastomer material intended for forming the receiving wall is integrally formed (e.g., overmolded, co-molded) onto a wall portion of the breathing mask device, and is lifted or separable from this wall portion to form the gel receiving chamber.

As a result, it becomes advantageously possible to create a breathing mask device that includes a gel structure that is especially effective with a view to an advantageous transmission of the mask forces. The gel structure can be formed by introducing the gel material into a gel receiving chamber, defined at least in some portions by an elastomer wall, for furnishing the gel receiving chamber. The elastomer wall is lifted or separable from a portion of the breathing mask device that functions as a mold wall in the context of the injection of the elastomer material.

In an embodiment of the invention, the gel receiving chamber is embodied such that it functions as a bracing bead portion. The bracing bead portion is preferably embodied such that it extends between the body structure of the breathing mask device and a user's face sealing lip of the breathing mask device. The bracing bead portion may be embodied such that it extends over the entire circumference of the sealing lip device. Preferably, however, the bracing bead portion is embodied in segmented fashion, such that it extends only in the contact region of the user's face sealing lip laterally bordering the nose. In the region of the sealing lip device that crosses the bridge of the nose as well as the upper lip region (in the case of a nose mask) or the chin region (full-face mask), embodying the gel structure can be dispensed with. As an alternative to completely dispensing completely with the gel structure in the aforementioned portions, it is also possible to embody the gel structure as recessed, in such a way that in the region of the bridge of the nose and in the upper lip or chin region, it transmits no bracing forces, or at least not any major or substantial bracing forces.

In an embodiment of the invention, the user's face sealing lip is embodied integrally with the wall that forms the receiving wall of the gel structure. Binding the user's face sealing lip to the remaining region of the sealing lip device may be accomplished in such a way that excessively high contact pressures resulting from the intrinsic rigidity of the user's face sealing lip or of the peripheral structure provided for binding the user's face sealing lip are generated. This mechanical behavior can be attained, e.g., by using suitably low Shore hardnesses and by suitably adapting the wall thicknesses and the three-dimensional curvature of the user's face sealing lip.

In an embodiment of the invention, the body structure is embodied as a so-called hard mask shell. The hard mask shell may be made from a completely transparent thermoplastic plastic material (e.g., polycarbonate). The hard mask shell may have connection structures (e.g., an inlet or elbow) for connecting a breathing gas line, particularly in the form of a flexible hose. The hard mask shell may also include gas washout devices that enable an adequate washout of used breathing gas out of the breathing mask interior to the environment.

In an embodiment of the invention, the sealing lip device is injection-molded onto this hard mask shell. Before the injection-molding of the sealing lip device onto it, the hard mask shell is preferably treated in such a way that it has locally demarcated reactive zones that are capable of adhesion, so that in these reactive zones the injected material bonds with high-strength adhesion to the body structure. These reactive zones may in particular be brought about by a corona or plasma treatment of the appropriate or selected regions of the hard mask shell. Alternatively to this, or in combination with this provision, it is also possible to create these locally demarcated reactive zones by applying adhesion promoters or by some other suitable treatment of the hard mask shell. The material comprising the hard mask shell, the type of zones intended for embodying an adhesive bond, and the properties of the elastomer material injection-molded onto the hard mask shell are preferably adapted such that the effect sought of a sufficiently heavy duty local bond between the elastomer material and the material of the hard mask shell is attained. The regions in which an excessively strong adhesion of the injected elastomer material to the hard mask shell is not wanted may optionally be locally suitably shielded by the application of parting means or a template or mask.

In an embodiment of the invention, in the region in which the elastomer wall for later embodying the gel receiving structure, the hard mask shell is defined such that by means of the hard mask shell, an advantageous fundamental geometry of this elastomer wall is already assured. In particular, the applicable portion of material can be injection-molded onto a bulging wall portion of the hard mask shell. Once the applicable elastomer material portion has been lifted from the bulging wall portion of the hard mask shell, a suitably large receiving chamber for the gel material is then created by cupping. The gel material may be introduced with a certain overpressure into the gel material receiving chamber intended for receiving the gel material and can in the process widen the elastomer wall. The geometry of the elastomer wall is preferably adapted such that at the latest in the widened state of the elastomer wall, the desired geometry of the gel structure is attained.

It is possible to provide filling conduits or fill valve structures on the sealing lip device or preferably in particular on the hard mask shell, by way of which conduits or structures of the gel receiving chamber intended for receiving the gel material can be filled. It is possible directly by means of the introduction of the gel material to lift or separate the wall, locally suitably injection-molded first onto the hard mask shell, by means of the gel material, so that the gel receiving chamber is accordingly generated gradually (blown up or expanded) in the course of the introduction of the gel. This introduction of the gel material can be done even before the complete unmolding of the mask device.

Another aspect of the invention is directed to a sealing lip device for a breathing mask with a gel structure having a gel body and an elastomer jacket surrounding the gel body in at least some portions; in the context of an injection-molding operation, the jacket is formed by injection molding of the elastomer material onto an opposite wall, and jacket is lifted or separated from this opposite wall in the course of the introduction of the gel material. The opposite wall forms part of a hard mask shell made from a substantially rigid plastic material. The opposite wall may also be furnished by means of an elastomer structure formed in the context of a preceding injection step.

Another aspect of the invention is further directed to a method for producing a breathing mask device. According to the method, in successive production steps, a breathing mask device is formed that includes a body structure and a sealing lip device. The sealing lip device is formed by injection of an elastomer material in portions onto the body structure in a mold chamber of a molding tool. The body structure is prepared, in a method step that may precede the elastomer material injection step, such that adhesion zones are created, in which the elastomer material (later) injected onto the hard shell enters into an adhesive bond with the body structure. The injection is also done in such a way that detachment zones are created, in which the injection elastomer material can be lifted from the body structure.

Another aspect of the invention is directed to a method for producing a breathing mask device having a body structure and a sealing lip device, wherein the method comprises forming at least one adhesion zone on the body structure, injection-molding the sealing lip device with an elastomer material onto the body structure in a suitable mold chamber, forming an adhesive bond between the body structure and the sealing lip device in each adhesion zone; and creating detachment zones in which the injected elastomer material of one or more portions of the sealing lip device is detachable from the body structure.

The adhesion zones, in an embodiment of the method, are generated by corona or plasma treatment. This corona or plasma treatment is performed in particular, after only partial unmolding of a molding tool intended to form the hard mask shell, by introducing a mask device into the molding tool and performing a locally defined and selective treatment of (only) certain portions of the hard mask shell. As an alternative to plasma or the corona treatment or in combination with this provision, it is also possible to treat the hard mask shell locally with suitable adhesion promoters.

The detachment zones, that is, the zones in which the elastomer material can be detached quite easily from the hard shell, are preferably already generated by the basic properties of the material provided for forming the hard shell. If needed, however, it is possible, in the vicinity of the corresponding adhesion zones, to shield or mask the regions of the hard shell that will later function as detachment zones, in such a way that the elastomer material injected onto them will not enter into an excessively strong adhesive bond with the hard mask shell. In this respect it is possible in particular to generate the detachment zones by the application of parting means (a shield, mask or template). Applying the parting means can be done using shielding baffles, by means of spray application, or by printing, in particular screen printing.

Lifting or separating the elastomer material injection-molded onto the detachment zones preferably forms a receiving chamber, into which a cushioning filling is introduced. This cushioning filling may be formed by a gas, in particular easily compressed ambient air; a foam material; or as mentioned several times above, a viscous material, in particular silicone gel.

According to another embodiment of the invention, there is provided a multi-part molding tool for forming a mask including a body portion and a sealing lip device, comprising a first mold segment; a second mold segment adapted to be positioned with respect to the first mold segment to form a first mold cavity having a first portion with a shape that matches a first portion of the body portion; a third mold segment adapted to be positioned with respect to the first and second mold segments to further define a second portion of the first mold cavity that has a shape that matches a second portion of the body portion; and a fourth mold segment to replace the third mold segment, the fourth mold segment being arranged with respect to the first and second mold segments and the then-formed body portion to define a second mold cavity having a shape matching a first portion of the sealing lip device.

These and other aspects of the invention will be described in or otherwise apparent from the following detailed description of embodiments.

BRIEF DESCRIPTION OF THE DRAWINGS

Further details and characteristics of the invention will become apparent from the ensuing description in conjunction with the drawings. Shown are:

FIGS. 2b-1, 2b-2, 2b-3, perspective sketches illustrating the portions, used as adhesion zones, of the hard shell element of FIG. 2a;

FIG. 3, a cross-sectional sketch illustrating the production of the breathing mask device of an embodiment of the invention, in a state immediately after the injection-molding of the elastomer material, intended to form the sealing lip device, onto the hard shell element;

DETAILED DESCRIPTION OF EMBODIMENTS

Figure 1:
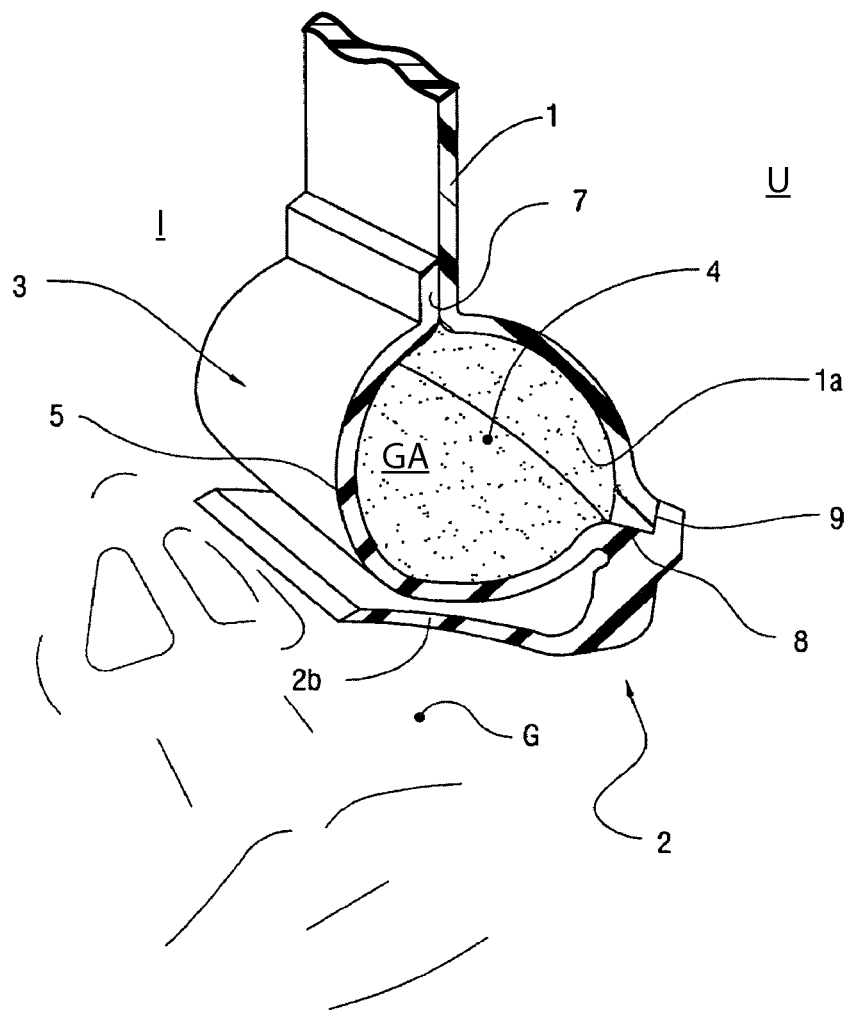
FIG. 1, a sectional sketch explaining the makeup of a breathing mask device according to an embodiment of the invention, in the region of the sealing lip device thereof.

A portion of a simplified breathing mask device is shown in FIG. 1 and includes a body structure or mask frame 1 and a sealing lip device 2 coupled with the body structure. By means of the body structure 1 and the sealing lip device 2, a breathing mask interior I is sealed off from the environment U, in cooperation with a user's face area G, shown here only schematically and not exactly to scale.

The breathing mask device shown here is distinguished by the fact that a gel structure 3 is provided, and the gel material 4 that forms this gel structure is received in an elastically deformable receiving wall 5 or jacket. This receiving wall 5 is made by integrally forming the elastomer material, provided for forming the receiving wall 5, onto a wall portion 1a, and this material is lifted or separated from the wall portion 1a for forming the gel receiving chamber GA that receives the gel material 4.

The gel receiving chamber GA forms a bracing bead portion that braces the breathing mask device on the area G of the user's face on which it rests. The bracing bead portion extends between the body structure 1 and a highly elastic, preferably relatively thin-walled user's face sealing lip 2b of the sealing lip device 2, and in the application position of the mask can be seated on the inside of the user's face sealing lip 2b, or optionally on the area of the user's face it is intended to rest on.

The user's face sealing lip 2b and the receiving wall portion 5 that in portions defines the gel receiving chamber GA are thus embodied integrally to this extent.

The body structure 1 is preferably embodied as a hard mask shell made of a fully transparent thermoplastic plastic material. It includes connection structures, not shown further here, for connecting breathing gas lines or valve devices.

The sealing lip device 2 is injection-molded onto this hard mask shell, as will be described in further detail hereinafter. In the state shown here in FIG. 1, the sealing lip device 2 is seated on adhesion zones 7, 8, 9, thus making a heavy-duty adhesive bond, which are formed by corona or plasma treatment of the hard mask shell. The wall portion 1a of the hard mask shell forms a detachment zone from which the material intended for forming the receiving wall 5 is lifted or separated from the wall portion 1a.

The production of the breathing mask device shown here can be done as described hereinafter.

Figure 2A:
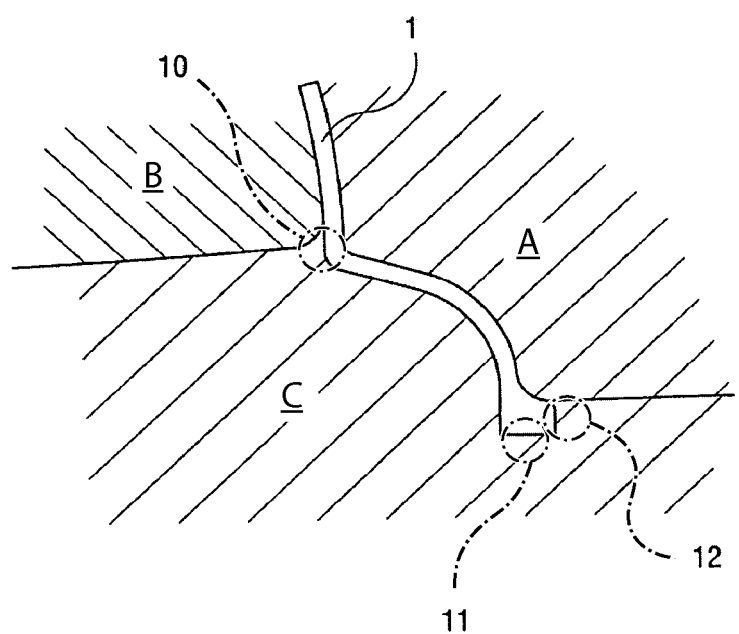
FIG. 2a, a sketch for explaining a hard shell component of the breathing mask device of FIG. 1.
Figures 1, 2B:
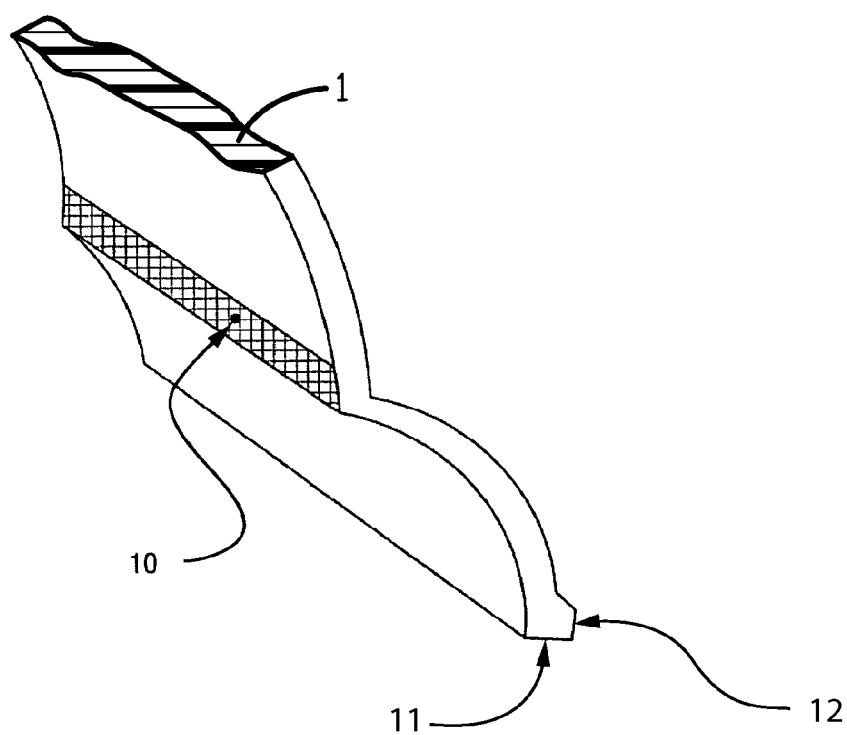
Figures 2, 2B:
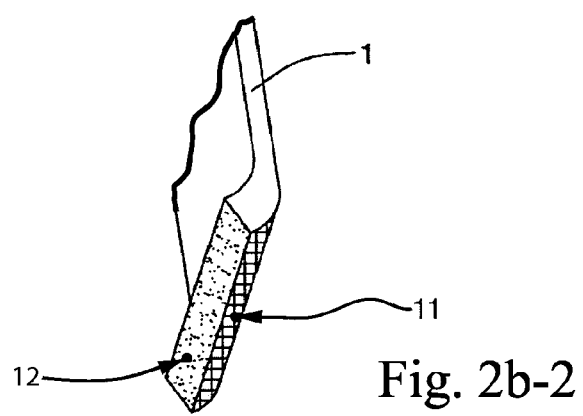

In FIG. 2a, a multi-piece molding tool is furnished, which in a first mold closing state furnishes a mold chamber intended to form the body structure 1 or the hard mask shell. This multi-part molding tool is shown here broken down merely as an example into mold segments A, B, C. Once the preferably thermoplastic plastic material intended for forming the hard shell has been injected into the mold chamber of the molding tool, and the plastic material has hardened sufficiently, the molding tool is opened by removing the core segment C. Next, preferably using a covering mask, adhesion zones 10, 11, 12 are embodied on the body structure 1 by corona or plasma treatment or some other kind of reactive treatment of the hard mask shell that otherwise still remains in the molding tool. In FIG. 2b, these adhesion zones 10, 11, 12 are shown in further detail.

Figures 2, 2B, 3:
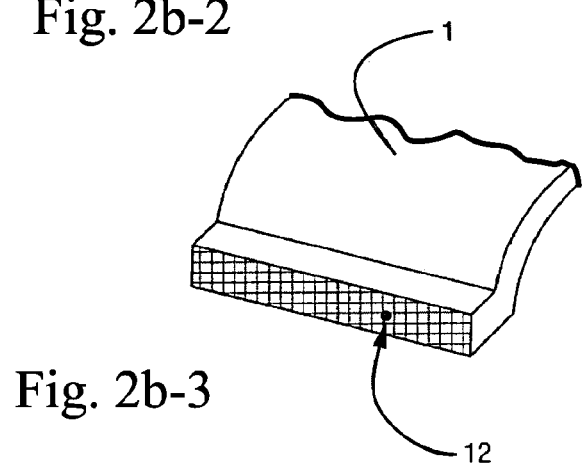
Figure 3:
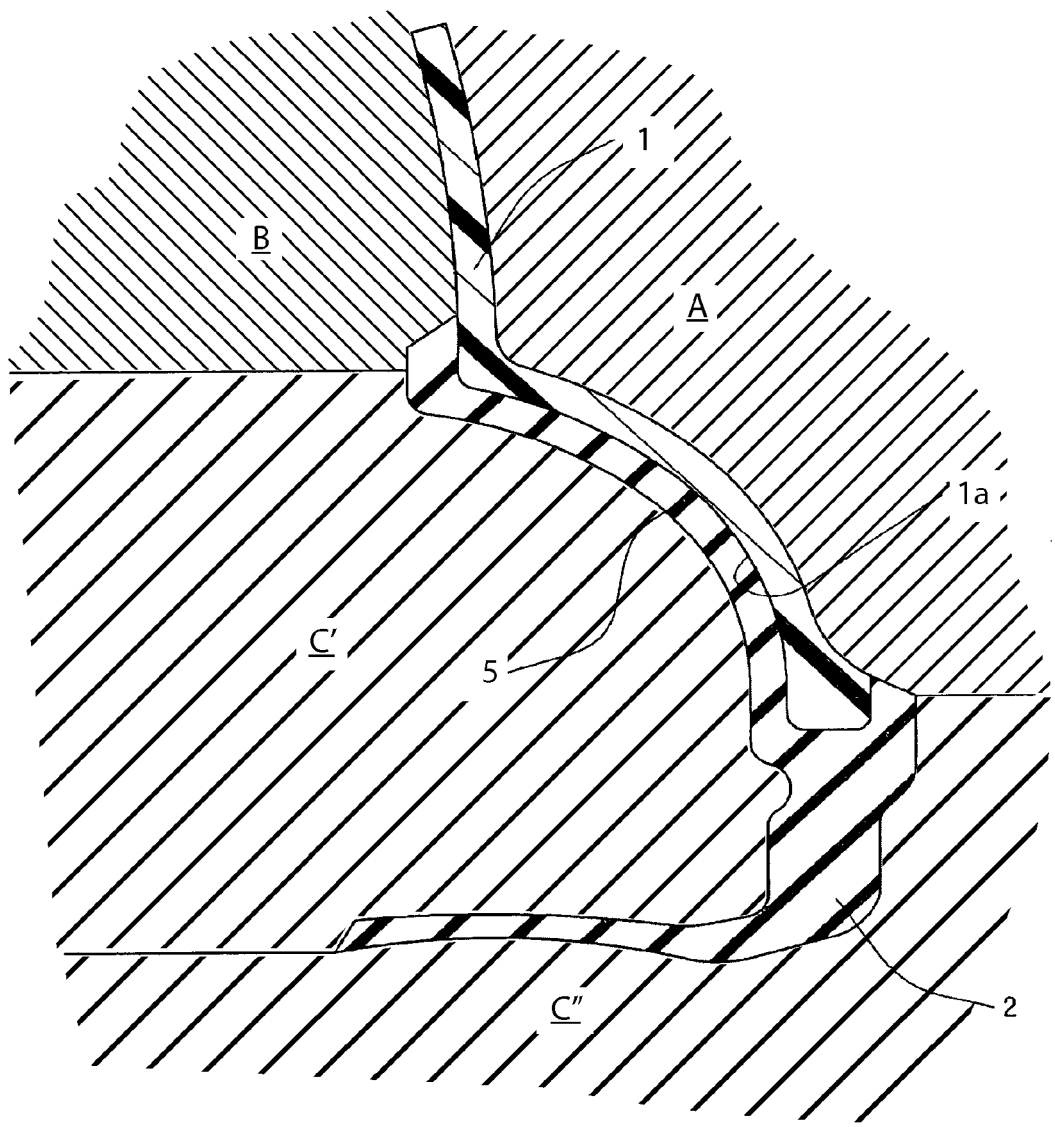

Next, instead of the mold segment C, a core segment C' and/or C", which is preferably again in multiple parts, is inserted into the molding tool as shown in FIG. 3. By means of this mold segment, a mold chamber intended for forming the sealing lip device 2 is furnished. An elastomer material, preferably liquid silicone rubber (LSR), is now injected into this mold chamber. This silicone material now enters into a firmly adhesive bond with the material of the hard mask shell, in the zones 10, 11, 12 sketched in FIGS. 2a, 2b-1, 2b-2, and 2b-3. In the wall portion 1a of the body structure (e.g., hard shell 1 adjacent to the wall 5, the silicone material is merely adjacent to or in contact with the wall portion 1a, but the silicone material is not bonded or is only slightly bonded to the wall portion 1a. The breathing mask device thus formed and including the body structure 1 or hard shell element and the sealing lip device 2 injection-molded onto it can be removed from the molding tool by suitable opening of the molding tool. By forcing a viscous medium, especially of silicone gel, into the boundary region defined between the receiving wall 5 and the body structure (e.g. hard shell) 1, it becomes possible to lift the receiving wall 5 gradually from the body structure 1 and in the process gradually to form the gel structure 3 (see FIG. 1).

Figure 4:
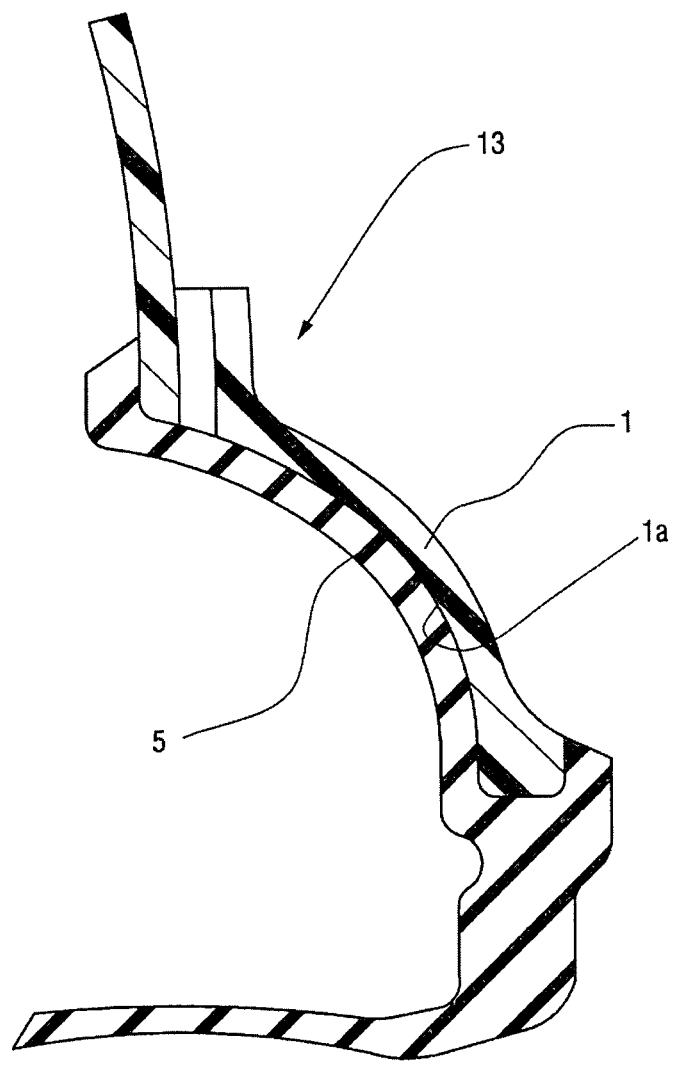
FIG. 4, a sketch illustrating a filling portion for filling the hard mask shell with the gel material according to an embodiment of the present invention.

As can be seen from FIG. 4, it is possible to provide a filling stub structure 13 on the body structure (e.g., hard shell) 1, through which the gel material can advantageously be introduced. Introducing the gel material and the detachability of the elastomer material injection-molded onto the body structure (e.g., hard shell) in the region of the wall portion 1a can be reinforced by special surface properties in the region of the wall portion 1a and in particular also by means of flat preferential conduit geometries. The filling stub structure 13 can be embodied in such a way that it is advantageously closable, in particular in automated fashion. The closing can be done in particular by means of a screw, plug or peg structure.

Figure 5:
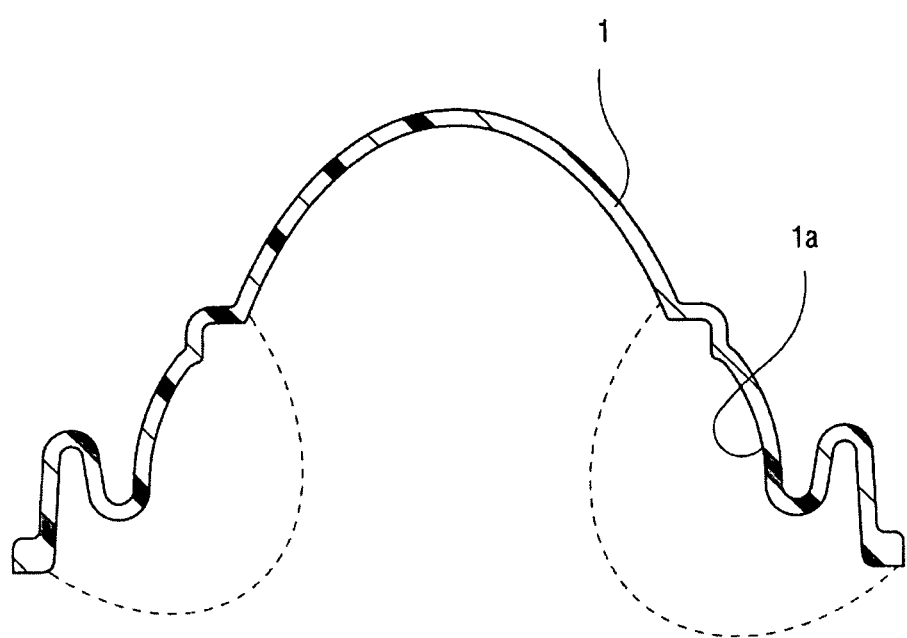
FIG. 5, a cross-sectional sketch explaining a preferred makeup of a hard shell element for furnishing large enough injection-molded wall portions according to an embodiment of the present invention.

FIG. 5 sketches a concept by which an "enlarged wall portion" 1a is created on the hard shell 1 or body structure, specifically by designing the cross section of the body structure 1 such that it has a strutlike or wavy form. The wall initially injection-molded onto the wall portion 1a here can then be lifted from this wall portion 1a, and in the corresponding cross section has essentially the same developed area, or length/width, as the length/width of the supporting wall 1a.

Figure 6:
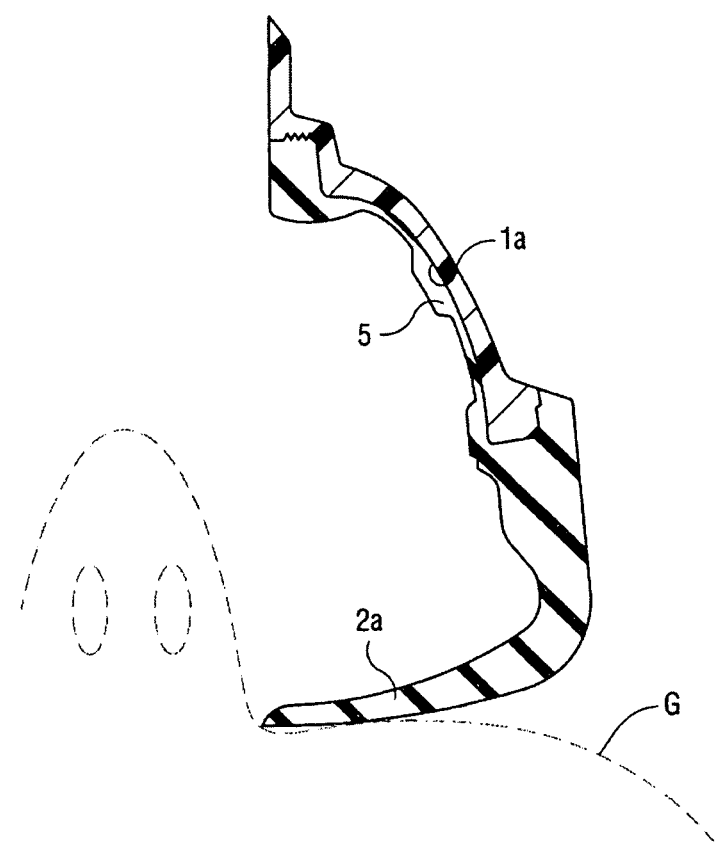
FIG. 6, a further cross-sectional sketch explaining details of the generation according to an embodiment of the invention of the gel structure.

FIG. 6 shows a cross-sectional sketch in which the wall 5 injection-molded onto the wall portion 1a has different wall thicknesses. Adapting these wall thicknesses makes it possible to exert influence on the mechanical properties of the gel structure that is finally to be formed in cooperation with the wall 5. The mechanical properties of the sealing lip device 2a resting on the area G of a user's face can also be defined by special designing of the course of the wall thickness and of the profiling of the sealing lip device.

Figure 7A:
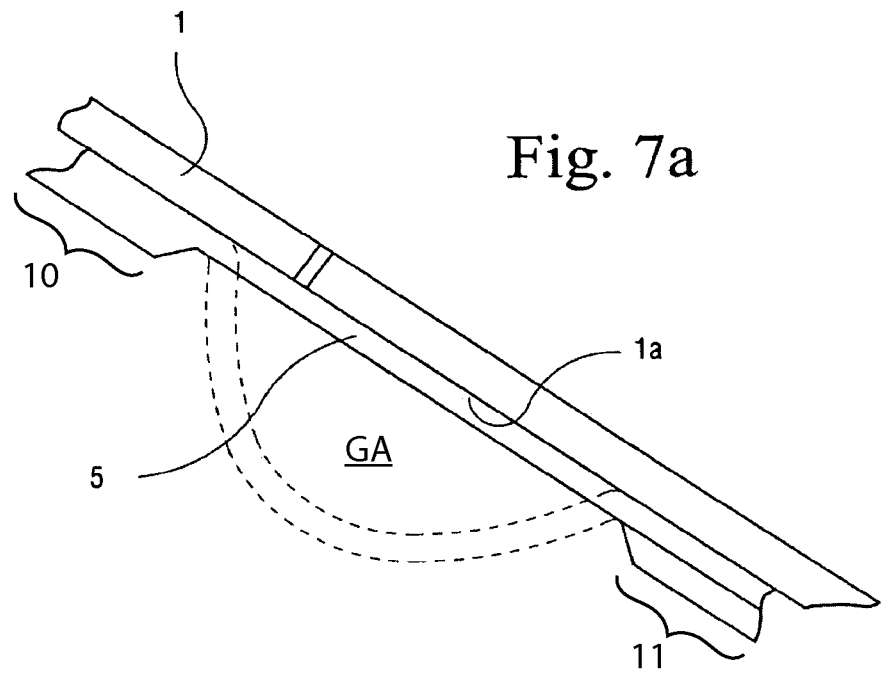
FIG. 7a, a basic sketch explaining the employment of the concept of an embodiment of the invention in the pairing of hard and elastomer materials.

As shown in sketchlike form in FIG. 7a, an embodiment of the invention for forming a gel receiving chamber GA can be realized especially advantageously by making a rigid/elastomer pairing of materials. Reactive zones 10, 11 are embodied on the body structure rigid structure) 1. The elastomer material is initially injection-molded over the full area of the body structure (e.g., rigid structure) 1 and in the process forms the wall 5 contacting the wall portion 1a. By introduction into the boundary region between the wall 5 and the supporting portion 1a, it becomes possible to inflate the wall 5 into the state represented here by dashed lines and as a result to create a gel-reinforced bead.

Figure 7B:
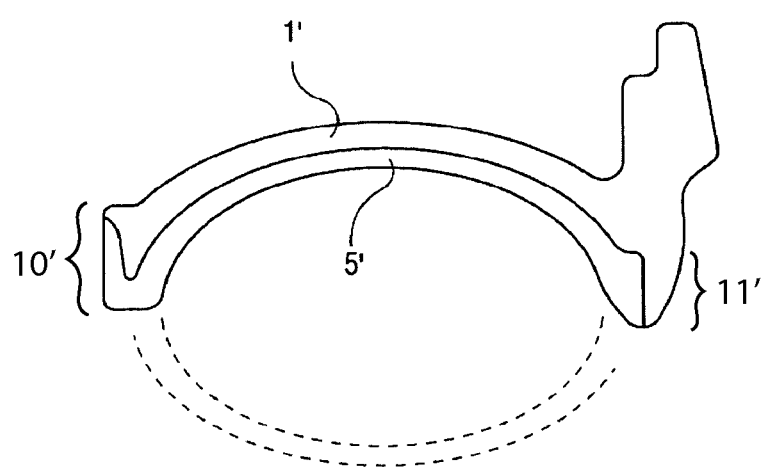
FIG. 7b, a sketch explaining the concept of an embodiment of the invention in pairing of elastomer/elastomer materials.

In FIG. 7b, a variant is shown in sketchlike form in which an embodiment of the invention is realized with a pairing of soft/soft or elastomer/elastomer materials. A second elastomer layer 5' is injection-molded onto the structure 1', here embodied of an elastomer material. Before the second injection step, intended for forming the wall 5', is performed, the structure 1' is pretreated in such a way that it includes reactive zones 10', 11'. By introducing a viscous medium, in particular silicone gel, into the gap region formed between the wall portions 1', 5', it becomes possible to create the inflated cushioning structure represented here by dashed lines.

Figure 8:
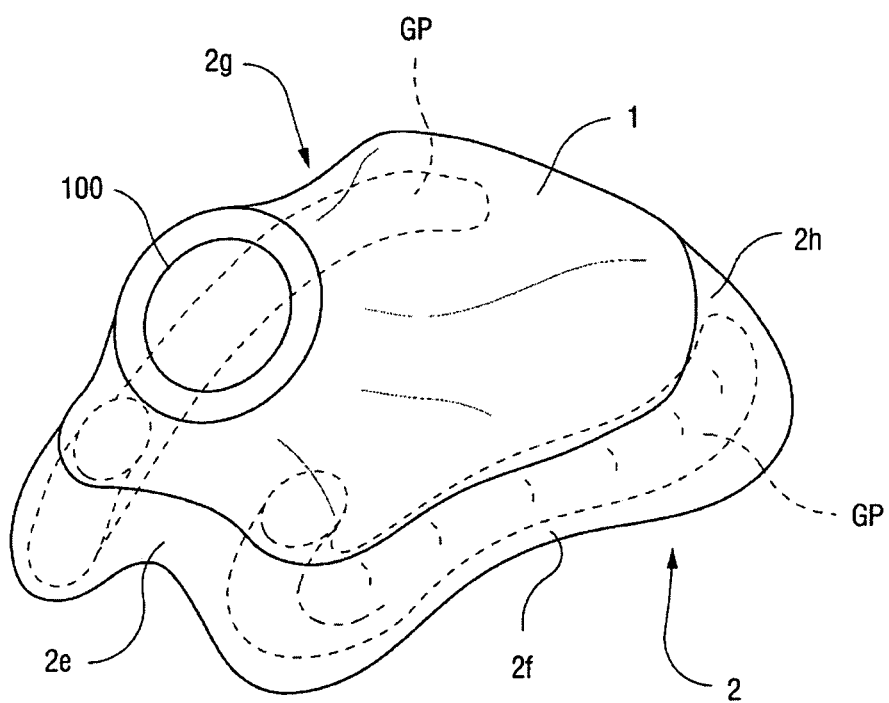
FIG. 8, a perspective sketch illustrating a breathing mask device according to an embodiment of the invention that includes a body structure, e.g., a hard shell element, and an elastomer sealing lip device injection-molded onto it, in which the sealing lip device in cooperation with the body structure forms two finger-like receiving chamber portions, into which a gel material is introduced, forming gel bead portions.

FIG. 8 in sketchlike form shows a breathing mask device according to another variant. This breathing mask device includes the body structure 1, which is embodied here as a completely transparent hard shell. The body structure 1 forms a connection opening 100 for connecting a line device serving to deliver breathing gas.

A sealing lip device 2 is injection-molded onto the body structure 1. The sealing lip device 2 is embodied such that it includes a bridge portion 2e, crossing the bridge of a user's nose, side portions 2f, 2g, and a lower bridge portion 2h crossing the upper lip or the chin region of the user. In the regions 2f, 2g, the sealing lip device 2 has a cross section that is approximately equivalent to the makeup shown in FIG. 1. In the region of the bridge portion 2e, the breathing mask device shown here has no gel structure. In the regions 2f and 2g, two beadlike gel cushions GP are provided, extending in beadlike form and, in the application position, along the side surface of the nose. These gel cushions GP are bounded partly by the body structure 1 and partly by the wall 5 that points toward the sealing lip 2b (see FIG. 1) and have a three-dimensionally greatly curved, finger-like course.

Figure 9A:
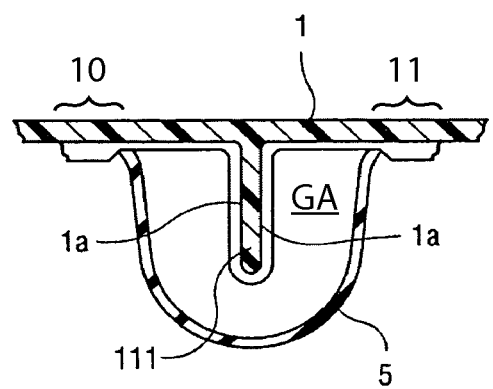
FIG. 9a, a basic sketch illustrating relatively large-area detachment zones according to an embodiment of the present invention.

In FIG. 9a, a variant is illustrated by which it becomes possible to furnish an enlarged injection-molding surface 1a for the embodiment of the wall 5. This is achieved by embodying a strut 111 on the body structure (e.g., structural component) 1. This strut, after the detachment of the wall 5 from the strut 111, dips into the gel receiving chamber GA. The strut 111 can damp the shifting of gel material in the gel receiving chamber and can thus influence the mechanical properties of the gel cushion. The strut 111 may be embodied to function as an end stop and prevents excessive deformation of the gel cushion. The definition of the region of the elastomer material, which serves as a gel chamber wall, is attained in this variant as well by embodying reactive zones 10, 11, on the injection-molding contact face toward the body structure 1, which zones assure a sufficiently strong adhesion of the gel material to the body structure (e.g., structural part) 1.

Figure 9B:
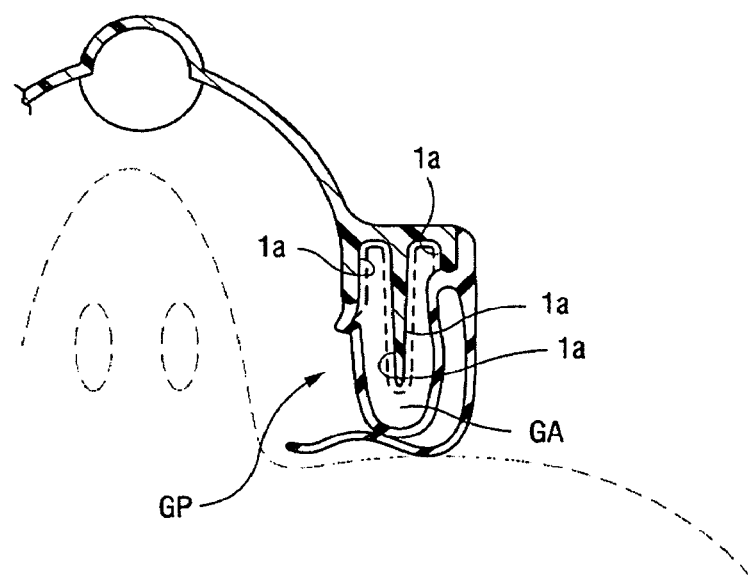
FIG. 9b, a basic sketch illustrating a breathing mask sealing lip according to an embodiment of the present invention.

FIG. 9b shows a gel cushion of a breathing mask according to an embodiment of the present invention. This gel cushion may extend all the way around the entire circumference of the sealing lip, or it may be provided as gel segments in only some portions. Such gel segments preferably extend within the portion of the sealing lip device that is provided for resting on the cheek region. The gel material may be viscous, or in other words fluid, or partly crosslinked, or in other words may be very resilient. Other kinds of filling materials can also be introduced into the receiving chamber GA. These materials are preferably colored such that they lend the mask an aesthetically appealing external appearance.

Figure 9C:
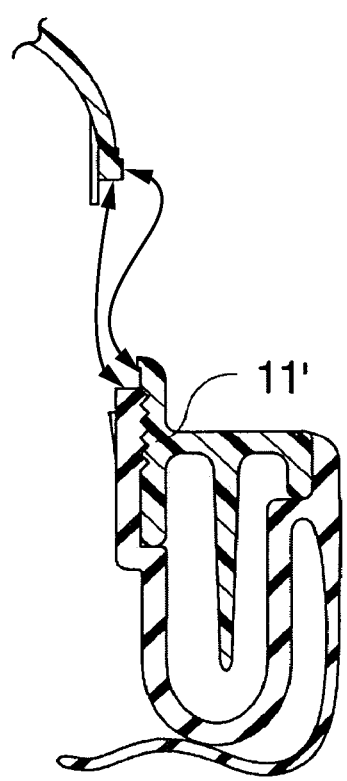
FIG. 9c, a basic sketch illustrating a frame element that can be placed in a sealed fashion against a further mask structure according to an embodiment of the present invention.

FIG. 9c shows an embodiment of the invention that can be realized in combination with a frame element 11'. By using the elastomer material, sealing structures, e.g., saw tooth region 11', can also be made, which serve to seal off and optionally secure the thus-created sealing structure to a mask body or other kind of carrier system.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Alternatively, further embodiments may include a single component or subportion thereof of any given embodiment. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

The invention claimed is:

1. A breathing mask device for administering a breathable gas, comprising:

a sealing lip device structured to seal against a contact surface of a user's face in use;

a body structure that, in combination with the sealing lip device, in part defines a breathing mask interior;

a gel structure for at least one of intermittent and partial transmission of retention forces, acting on the body structure, to the user's face; and a gel material defining the gel structure is received in a gel receiving chamber defined at least in part by the body structure and an elastically deformable receiving wall that is attached to the body structure at at least two locally defined reactive zones,
wherein the elastically deformable receiving wall is integrally formed onto a wall portion of the body structure at the at least two locally defined reactive zones of the breathing mask device, such that the elastically deformable receiving wall is conformable to the wall portion of the body structure, and
wherein said elastically deformable receiving wall is separated from the wall portion between the at least two locally defined reactive zones to form the gel receiving chamber when the gel material is inserted between the elastically deformable receiving wall and the wall portion of the body structure.

2. The breathing mask device of claim 1, wherein the gel receiving chamber comprises a bracing bead portion.

3. The breathing mask device of claim 2, wherein the bracing bead portion extends between the body structure and a user's face sealing lip.

4. The breathing mask device of claim 3, wherein the user's face sealing lip and the receiving wall of the gel structure are integrally formed.

5. The breathing mask device of claim 1, wherein the body structure comprises a hard mask shell or frame element.

6. The breathing mask device of claim 5, wherein the sealing lip device is injection-molded onto the hard mask shell or the frame element.

7. The breathing mask device of claim 6, wherein before the injection molding of the sealing lip device, the locally defined reactive zones are generated on the element that forms the body structure.

8. The breathing mask device of claim 7, wherein the reactive zones are generated by corona or plasma treatment.

9. The breathing mask device of claim 7, wherein the reactive zones are generated by adhesion promotion.

10. The breathing mask device of claim 7, wherein the reactive zones intended for detachment of the gel material are locally shielded.

11. The breathing mask device of claim 1, further comprising a filling conduit structure provided on the body structure.

12. A sealing lip device for a breathing mask having a body structure, the sealing lip device comprising:
a gel structure having a gel body; and
an elastomer jacket surrounding at least a portion of the gel body,
wherein the elastomer jacket is formed by injection molding the elastomer jacket onto an opposite wall of the body structure, and
wherein a conforming portion of the elastomer jacket is separable from the opposite wall to form a gel material receiving chamber.

13. A method for producing a breathing mask device having a body structure and a sealing lip device, wherein the method comprises:
forming at least two adhesion zones on the body structure;
injection-molding the sealing lip device with an elastomer material onto the body structure in a suitable mold chamber;
forming an adhesive bond between the body structure and the sealing lip device in each adhesion zone; and
creating at least one detachment zone between the at least two adhesion zones in which a portion of the elastomer material of the sealing lip device is detachable from a corresponding portion of the body structure,
wherein each at least one detachment zone of the elastomer material conforms portion of the body structure from which it is detachable.

14. The method of claim 13, further comprising generating the adhesion zones by corona or plasma treatment.

15. The method of claim 13, further comprising generating the adhesion zones by applying adhesion promoters.

16. The method of claim 13, wherein the at least one detachment zone is caused by or results from basic properties of the material comprising the body structure.

17. The method of claim 13, further comprising generating the at least one detachment zone by applying parting means.

18. The method of claim 13, wherein a receiving chamber for receiving a cushioning filling is formed by lifting the elastomer material in a region of the at least one detachment zone.

19. The method of claim 18, wherein the cushioning filling is formed by a gas or air.

20. The method of claim 18, wherein the cushioning filling is formed by a viscous medium.

21. The method of claim 18, wherein the cushioning filling is formed by a foam material.

22. The method of claim 18, wherein the lifting of the elastomer material is effected by introducing the filling material.

23. The breathing mask device of claim 1, wherein the body structure comprises a thermoplastic material, and wherein the sealing lip device and the gel structure comprise an elastomeric material.

24. The breathing mask device of claim 1, wherein said receiving wall, in an undeformed state, is substantially conformed with the wall portion.

25. The breathing mask device of claim 1, wherein said gel receiving chamber is located between the at least two locally defined reactive zones.

26. A mask to administer breathable gas to a user, the mask comprising:
a sealing lip to seal against the user's face;
a body structure;
a chamber defined by a wall and the body structure; and
at least two adhesion zones attaching the wall and the body structure to define the chamber,
wherein the wall is conformable to the body structure between the at least two adhesion zones, and
wherein the wall is separated from the body structure when a filler is introduced between the wall and the body structure.

27. The mask of claim 26, comprising the filler being contained within the chamber.

28. The mask of claim 27, wherein the filler is a gel material.

29. The mask of claim 27, wherein the filler is a gas.

30. The mask of claim 27, wherein the filler is a viscous medium.

31. The mask of claim 27, wherein the filler is a foam material.

32. The mask of claim 26, wherein the body structure comprises a hard mask shell or a frame element.

33. The mask of claim 32, wherein the sealing lip is injection-molded onto the hard mask shell or the frame element.

34. The mask of claim 33, wherein before the injection molding of the sealing lip, the adhesion zones are generated on the element that forms the body structure.

35. The mask of claim 34, wherein the adhesion zones are generated by corona or plasma treatment.

36. The mask of claim 26, further comprising a filling conduit structure provided on the body structure.

* * * * *

UNITED STATES PATENT AND TRADEMARK OFFICE
CERTIFICATE OF CORRECTION

PATENT NO.        : 8,684,003 B2
APPLICATION NO.   : 11/988503
DATED             : April 1, 2014
INVENTOR(S)       : Burz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1721 days.

Signed and Sealed this

Twenty-ninth Day of September, 2015

Michelle K. Lee
*Director of the United States Patent and Trademark Office*